United States Patent
Hung et al.

(10) Patent No.: US 9,900,677 B2
(45) Date of Patent: Feb. 20, 2018

(54) SYSTEM FOR CONTINUOUS MONITORING OF BODY SOUNDS

(71) Applicant: INTERNATIONAL BUSINESS MACHINES CORPORATION, Armonk, NY (US)

(72) Inventors: Li-Wen Hung, Mahopac, NY (US); John U. Knickerbocker, Monroe, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/974,860

(22) Filed: Dec. 18, 2015

(65) Prior Publication Data

US 2017/0180870 A1    Jun. 22, 2017

(51) Int. Cl.
*H04R 1/04*    (2006.01)
*A61B 5/02*    (2006.01)
(Continued)

(52) U.S. Cl.
CPC .............. *H04R 1/04* (2013.01); *A61B 5/02* (2013.01); *A61B 5/02028* (2013.01);
(Continued)

(58) Field of Classification Search
CPC .. H04R 19/04; H04R 29/004; H04R 2420/07; H04R 2201/003; H04R 1/04; H04R 19/016; A61B 5/02438; A61B 5/0816; A61B 2560/0412; A61B 5/113; A61B 7/04; A61B 5/02; A61B 2562/164; A61B 2562/166; A61B 2562/028
(Continued)

(56) References Cited

U.S. PATENT DOCUMENTS 5,856,914 A * 1/1999 O'Boyle ............... G01L 9/0073
361/761
6,178,249 B1 * 1/2001 Hietanen ............... H04R 19/005
367/181
(Continued)

FOREIGN PATENT DOCUMENTS

CN    103139691 B    3/2015
CN    104473628 A    4/2015
(Continued)

OTHER PUBLICATIONS

Mandal et al (A Battery-Free Tag for Wireless Monitoring of Heart Sounds; Body Sensor Networks, pp. 201-206, Jun. 2009: DOI10.1109/P3644.10).*

(Continued)

*Primary Examiner* — Davetta W Goins
*Assistant Examiner* — Oyesola C Ojo
(74) *Attorney, Agent, or Firm* — Tutunjian & Bitetto, P.C.; Louis J. Percello

(57) ABSTRACT

A wearable monitoring system includes a microelectromechanical (MEMS) microphone to receive acoustic signal data through skin of a user. An integrated circuit chip is bonded to and electrically connected to the MEMS microphone. A portable power source is connected to at least the integrated circuit chip. A flexible substrate is configured to encapsulate and affix the MEMS microphone and the integrated circuit chip to the skin of the user.

20 Claims, 3 Drawing Sheets

(51) Int. Cl.
*A61B 5/00* (2006.01)
*A61B 7/00* (2006.01)
*A61B 5/024* (2006.01)
*H04R 19/01* (2006.01)

(52) U.S. Cl.
CPC ...... *A61B 5/02438* (2013.01); *A61B 5/02444* (2013.01); *A61B 5/6833* (2013.01); *A61B 7/00* (2013.01); *A61B 5/0022* (2013.01); *A61B 2560/0214* (2013.01); *A61B 2560/0412* (2013.01); *A61B 2562/0204* (2013.01); *A61B 2562/028* (2013.01); *A61B 2562/0271* (2013.01); *A61B 2562/12* (2013.01); *A61B 2562/164* (2013.01); *A61B 2562/166* (2013.01); *H04R 19/016* (2013.01); *H04R 2201/003* (2013.01); *H04R 2420/07* (2013.01)

(58) Field of Classification Search
USPC .............................................. 381/113, 56, 58
See application file for complete search history.

(56) References Cited

U.S. PATENT DOCUMENTS

| | | | | |
|---|---|---|---|---|
| 6,754,472 | B1* | 6/2004 | Williams | H04Q 9/04 455/100 |
| 7,539,532 | B2 | 5/2009 | Tran | |
| 7,873,176 | B2 | 1/2011 | Pavlovic et al. | |
| 8,582,788 | B2 | 11/2013 | Leidl et al. | |
| 8,605,919 | B2 | 12/2013 | Awamura et al. | |
| 8,692,340 | B1* | 4/2014 | Ata | B81B 3/001 257/415 |
| 8,847,289 | B2 | 9/2014 | Wang | |
| 8,896,184 | B2 | 11/2014 | Grosh et al. | |
| 9,078,068 | B2 | 7/2015 | Langlois et al. | |
| 9,609,439 | B2* | 3/2017 | Agashe | H04R 23/008 |
| 2006/0008098 | A1 | 1/2006 | Tu | |
| 2008/0013747 | A1* | 1/2008 | Tran | A61B 7/04 381/67 |
| 2008/0164545 | A1* | 7/2008 | Hsiao | B81C 1/0023 257/416 |
| 2010/0217345 | A1* | 8/2010 | Wolfe | A61B 5/024 607/17 |
| 2010/0284553 | A1* | 11/2010 | Conti | B81B 7/0061 381/174 |
| 2011/0137144 | A1* | 6/2011 | Rofougaran | H04L 12/6418 600/407 |
| 2011/0137209 | A1* | 6/2011 | Lahiji | A61B 7/026 600/586 |
| 2011/0182447 | A1* | 7/2011 | Kim | H04R 27/00 381/151 |
| 2011/0184302 | A1* | 7/2011 | Eschler | A61B 5/08 600/529 |
| 2012/0209132 | A1* | 8/2012 | Jones | A61B 7/026 600/528 |
| 2012/0328132 | A1 | 12/2012 | Wang | |
| 2013/0161702 | A1 | 6/2013 | Chen | |
| 2014/0254837 | A1* | 9/2014 | Mortensen | H03F 3/187 381/120 |
| 2014/0370855 | A1* | 12/2014 | Koss | H04M 3/53366 455/413 |
| 2014/0378849 | A1 | 12/2014 | Krimsky et al. | |
| 2015/0060955 | A1 | 3/2015 | Chen | |
| 2015/0189444 | A1 | 7/2015 | Pan et al. | |
| 2015/0304751 | A1* | 10/2015 | Chen | H04R 19/005 381/361 |

FOREIGN PATENT DOCUMENTS

| | | |
|---|---|---|
| JP | 2000-316825 A | 11/2000 |
| KR | 200269580 Y1 | 3/2002 |
| WO | 2012/088688 A1 | 7/2012 |

OTHER PUBLICATIONS

Zhang, T.T. et al., "Sound Based Heart Rate Monitoring for Wearable Systems" 2010 IEEE International Conference on Body Sensor Networks (2010) pp. 139-143.

Turqueti, M. et al., "Smart Acoustic Sensor Array (SASA) System for Real-Time Sound Processing Applications" (Mar. 27, 2014) pp. 1-38.

Noma, H. et al., "Wearable Data Acquisition for Heartbeat and Respiratory Information Using NAM (Non-Audible Murmur) Microphone" Proceedings of the 2005 Ninth IEEE International Symposium on Wearable Computers (2005) pp. 1-2.

Wang, H. et al., "Heart Sound Measurement and Analysis System with Digital Stethoscope" 2nd International Conference on Biomedical Engineering and Informatics (2009) pp. 1-5.

Mandal, S. et al., "A Battery-Free Tag for Wireless Monitoring of Heart Sounds" IEEE 2009 Body Sensor Networks (2009) pp. 201-206.

Sezen, A.S. et al., "Passive Wireless MEMS Microphones for Biomedical Applications" J Biomech Eng (2005) pp. 1030-1034, vol. 127, No. 6.

MEMS Microphones, http://www.akustica.com/microphones.asp (2014) 1 page.

* cited by examiner though in the flexible substrate. A temperature sensor may be embedded into CMOS chip to monitor chamber temperature.

SYSTEM FOR CONTINUOUS MONITORING OF BODY SOUNDS

BACKGROUND

Technical Field

The present invention relates to body sound monitoring systems, and more particularly to systems and methods for monitoring the heart and other body parts using a low-profile, low cost wearable device.

Description of the Related Art

Continuous monitoring of heart activity provides useful medical information whether an individual is suffering from a heart ailment or simply desires information about their heart. Some research shows that an abnormal heart-rate profile during exercise and recovery may be a predictor of sudden death from heart failure. Abnormal heart sounds can reveal a possible fatal emergency such as congestion, value failure, heart tremble, etc. Continuous monitoring, periodic monitoring and/or regular trending of heart sounds for individuals under certain types of conditions or continuously can provide early detection of emerging cardio health problems.

SUMMARY

A wearable monitoring system includes one or more microelectromechanical (MEMS) microphone(s) to receive acoustic signal data through skin of a user. An integrated circuit chip is bonded to and electrically connected to the MEMS microphone. A portable power source is connected to at least the integrated circuit chip. A flexible substrate is configured to encapsulate and affix the MEMS microphone and the integrated circuit chip to the skin of the user.

Another wearable monitoring system includes a microelectromechanical (MEMS) microphone to receive acoustic signal data through skin of a user. An integrated circuit chip is bonded to and electrically connected to the MEMS microphone using flip chip technology. A flexible substrate is configured to encapsulate and affix the MEMS microphone and the integrated circuit chip to the skin of the user using an adhesive. A portable power source is connected to at least the integrated circuit chip including a battery-free tag formed on or in the flexible substrate for harvesting energy from radiofrequency signals.

A method for monitoring body sounds includes adhering a monitoring system to skin of a user using a flexible substrate to encapsulate and affix a MEMS microphone to receive acoustic signal data and an integrated circuit chip, which is bonded to and electrically connected to the MEMS microphone; powering the monitoring system using a portable power source disposed in or on the flexible substrate; monitoring the acoustic signal data of the user through the skin of the user; and storing the acoustic signal data on the integrated circuit chip.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
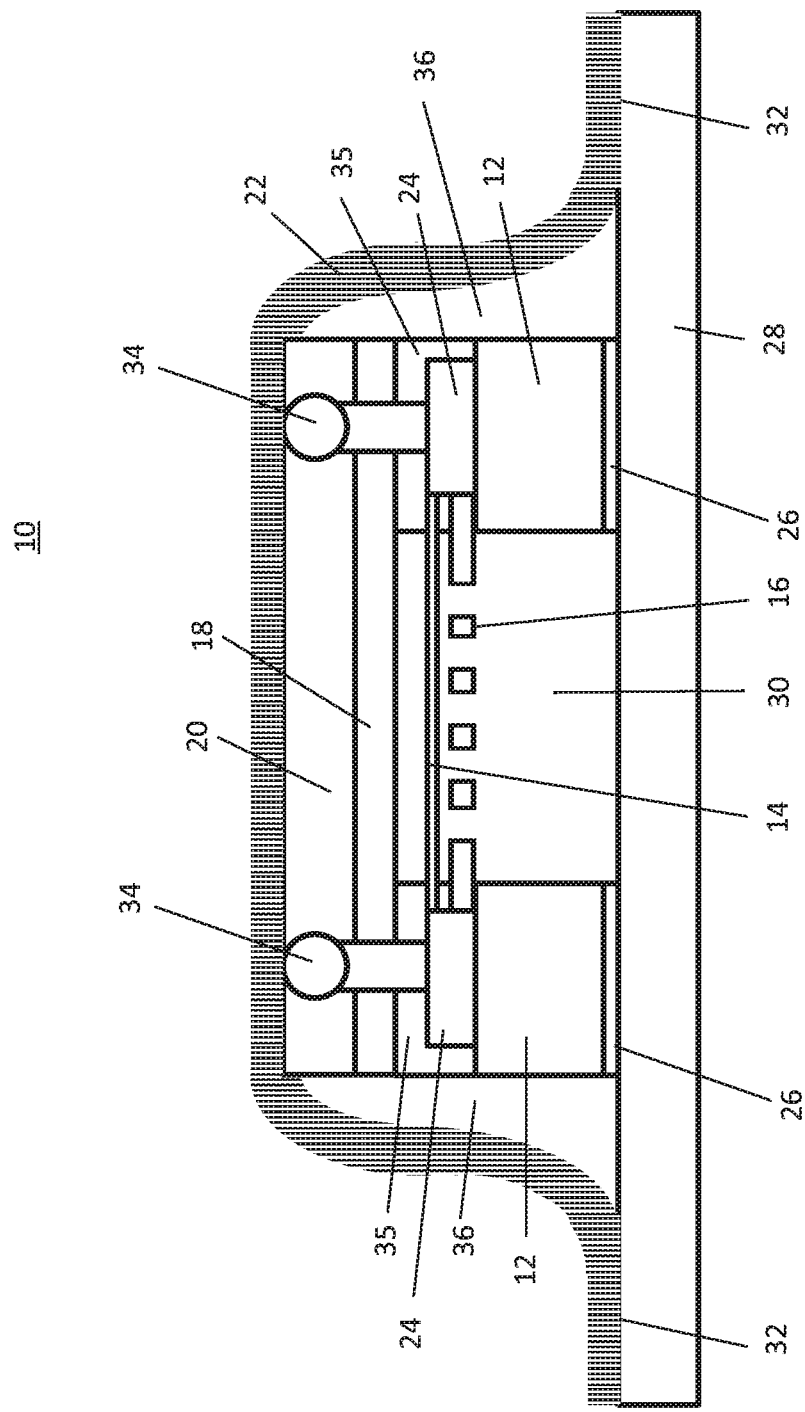
FIG. 1 is a cross-sectional view of a monitoring system for monitoring body sounds installed on a user's skin in accordance with the present principles.

In accordance with the present principles, systems and methods are provided for a wearable body sound monitoring device. The wearable device may be attached to the skin of a user and continuously monitor heart or body sounds of a user. The wearable device is low-profile and compatible with everyday activities. The wearable device may include a transmitter to transmit data to a remote receiver. The receiver may include a smart phone, computer or a processing center. The wearable device may include one or more microelectromechanical (MEMS) microphone chip(s). The MEMS chip(s) may be included in a system that attaches to the skin of the user to measure heart or body sounds. The system may include memory to store the data and may include signal processing capabilities. In other embodiments, an antenna is included in the system to transmit the data remotely. The signal processing and storage may be processed remotely as well.

The wearable monitoring system may include one or more MEMS microphones placed on the user. The wearable monitoring system includes a portable, wearable, disposable, rechargeable and/or alternate power source connected to the integrated circuit chip. A flexible substrate is configured to encapsulate and affix the MEMS microphone and the integrated circuit chip to the skin of the user and form a sound chamber.

MEMS technology may include commercially available chips from various manufacturers and be employed, e.g., in smart phones, tablets, etc. In one embodiment a battery-free tag may be employed for wirelessly monitoring heart sounds, e.g., an omnidirectional electret condenser microphone may be employed as an acoustic sensor and an antenna may be included to harvest energy from radiofrequency (RF) transmitters to power the system.

In one useful embodiment, a wearable system for continuous monitoring of heart or body sounds includes a micro-machined MEMS microphone, which can be a condenser/electrostatic, piezoelectric, or piezo-resistive device. A complementary metal oxide semiconductor (CMOS) chip for signal conditioning, power management, memory storage, and data transmission is coupled to the microphone. A flexible substrate provides adhesion to the skin of a user, supports the system to make it wearable and forms a sound chamber. An antenna and a thin film battery may be built into the flexible substrate. A temperature sensor may be embedded into CMOS chip to monitor chamber temperature. Another microphone may include electrostatic sensing where a perforated rigid plate is separated from a thin flexible diaphragm by a gap formed via removal of sacrificial material. The plate and diaphragm may be metal films or dielectric-metal composite films.

The system is employed to listen to and monitor heart and/or other body sounds. A plurality of systems may be employed on a same user to differentiate acoustic signal origins and acoustic signal directions. A footprint and cost of MEMS microphones is small enough that the system can be disposable and can be driven by portable electronics. Once the data of the body sounds is in digital form, adaptive filtering and amplification via signal processing methods can be applied to render cleaner data. Data of body sounds can then be presented audibly or visually to medical professionals, health care professionals, the user or designated individuals. Such data can enable computer-assisted diagnostics or first screening of possibly serious problems, such data can be encrypted to ensure privacy and security of the data and user or patient and can be stored locally, used in local computation/analysis and/or sent to data storage in the home, hospital, private practice or data center or cloud data space with any appropriate authorizations for access.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a non-volatile electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a phase change memory (PCM) device, a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a cross-sectional view of an exemplary embodiment for a wearable heart and body monitoring system 10 is illustratively shown for gathering acoustic information from a user in accordance with the present principles. System 10 includes a MEMS device 12 bonded to a CMOS chip 18. The CMOS chip 18 and the MEMS device 12 may be oxide bonded using an oxide layer 35. The MEMS device 12 functions as a MEMS microphone. The MEMS device 12 and the CMOS chip 18 are electrically connected by connections 24 using flip chip package technology. Connections 24 may include through silicon vias (24) that are terminated using solder balls 34.

The MEMS device/microphone 12 includes a MEMS circuit and may further include a flexible diaphragm 14 and a rigid perorated plate 16 for sound holes for the sound to pass through. The MEMS microphone/device 12 may include a condenser/electrostatic type device, a piezoelectric type device or piezo-resistive type device. In one embodiment, the MEMS device/microphone 12 includes electrostatic sensing where the perforated rigid plate 16 is separated from the thin flexible diaphragm 14 by a gap formed via removal of a sacrificial material.

The CMOS chip 18 faces (device side) downward toward the diaphragm 14. The CMOS chip 18 includes field effect transistors forming circuits for performing signal conditioning, power management, and data transmission. The CMOS chip 18 may include an application specific integrated circuit (ASIC) configured to receive, store and transmit data from the MEMS microphone/device 12 or other data sources. For example, a temperature sensor may be embedded into CMOS chip 18 to monitor a temperature of a chamber 30 and/or 36.

The MEMS device/microphone 12 may include contacts 26 that touch skin 28 of the user. The contacts 26 may include a corrosion resistant material or metal. The contacts 26 may also be employed for other purposes, e.g., measuring skin resistance, measuring contact pressure of the system 10, etc.

The solder bumps 34 may be encapsulated in an underfill material 20, which may include a resin (epoxy, polyurethane, etc.), or dielectric, such as silicon dioxide. A flexible substrate 22 is adhered to the underfill material 20. The flexible substrate 22 may include a polymeric material, (e.g., polyvinyl, polyethylene, etc.). The flexible substrate 22 extends over the CMOS chip 18 and the MEMS device 12 in one or more dimensions to make contact with the skin 28 of the user. The flexible substrate 22 may include adhesive 32 to adhere the flexible substrate 22 and the system 10 to the skin 28 of the user.

System 10 may be powered using a battery, a photovoltaic cell, a battery-free tag or other portable energy device. The battery-free tag may include an antenna on the flexible substrate 22 that is employed to harvest energy from RF transmitters to power the system. The RF transmitters may include energy from cell phones or dedicated wireless RF transmitters that may be fixed or portable to power the system 10. The flexible substrate 22 provides adhesion to the skin 28 all around the system 10 to form a sound chamber 36. In addition to an antenna, the flexible substrate 22 may include a thin film battery built onto or into the flexible substrate 22. The flexible substrate 22 is connected to the CMOS chip 18 through the underfill material 20. Connections may be made to the CMOS chip 18 and connected using solder bumps 34 and/or other metal connections.

In accordance with the present principles, the system 10 is adhered to a user. Upon activation, the system 10 begins to monitor heartbeat and/or other bodily sounds, e.g., bones cracking, breathing, digestive noise, joint impact noise, neck, head, teeth and brain sounds, blood flow in arms, hands, fingers, legs, feet, toes, etc. The heart sounds, etc. are employed to monitor health, status and/or functionality by analyzing the measured sound wave directly at the user's skin 28. The MEMS device 12 measures the acoustic waves, which are digitized and recorded or digitized and transmitted by the CMOS chip 18.

The CMOS chip 18 may be programmed to monitor the acoustic signals to determine changes or simply to collect data. The sound recording/monitoring system 10 includes a form factor suitable for wearing on the skin 28 throughout the day and/or night. The form factor is preferably no larger than 5 mm by 5 mm by 1.5 mm; however larger or smaller dimensions are contemplated, and in one useful embodiment, the system 10 is less than 1 mm in height (e.g., off the skin). The flexible substrate 22 may include a breathable fabric or may include a water resistant material.

The wearable system 10 is configured for continuous monitoring of heart or body sounds. The system 10 may be employed for medical monitoring, baseline monitoring, activity monitoring, informational monitoring, etc. The system 10 may be installed for hours, days, weeks or longer. The system 10 may be disposable, re-useable, partially disposable and partially re-useable. The system 10 may be combined with other sensor functions, data analysis and/or communications. The system 10 may be embedded in clothing or connected as a skin wearable patch. The system 10 may be connected or hardwired to or through clothing by, proximity wireless data, power transfer or wireless near field communication or power transfer. Due to the low profile, the system 10 may be left installed during sleep or other activities. The system 10 may have a timing element to correlate time and data to the users activities either manually or automatically with other integrated or correlated sensors such a accelerometers and position sensors to indicate standing, moving, sitting, laying down, etc.

Figure 2:
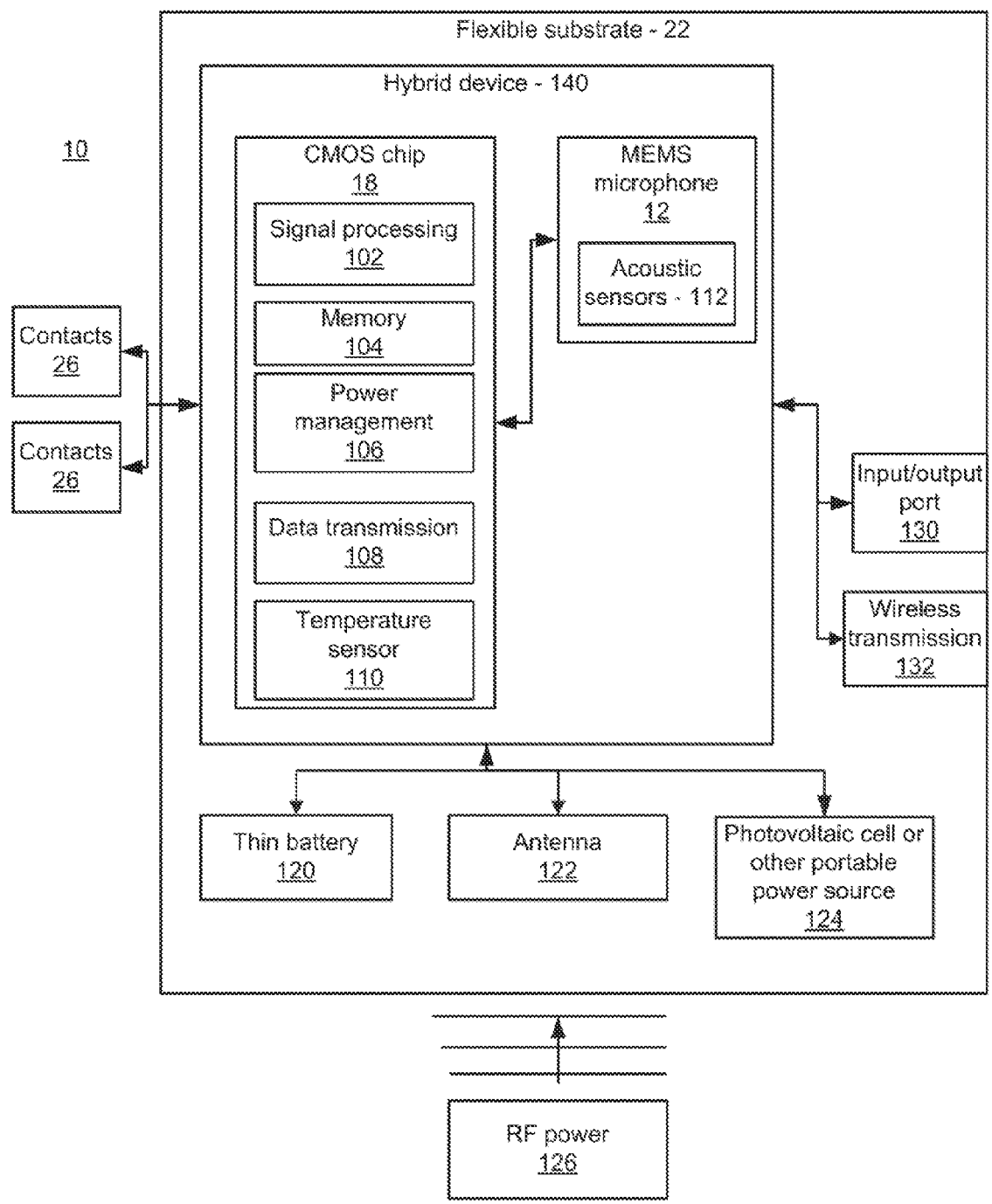
FIG. 2 is a block/flow diagram showing a schematic for a monitoring system for monitoring body sounds in accordance with the present principles.

Referring to FIG. 2, a schematic diagram illustratively depicts the system 10 in accordance with the present principles. System 10 includes a hybrid device 140 that includes a MEMS device 12 electrically connected to a CMOS chip 18. The MEMS device 12 and the CMOS chip 18 may be electrically connected using flip chip package technology.

The MEMS device 12 functions as a MEMS microphone and may include one or more acoustic sensors 112. The acoustic sensors 112 may include a flexible diaphragm and a rigid perforated plate for sound holes for the sound to pass through. The MEMS microphone/device 12 may include a condenser/electrostatic type device, a piezoelectric type device or piezo-resistive type device.

The CMOS chip 18 includes field effect transistors forming circuits for performing signal conditioning, power management, and data transmission. The CMOS chip 18 may include an application specific integrated circuit (ASIC) configured to receive, store and transmit data from the MEMS microphone/device 12 or other data sources. A signal processing circuit 102 of the CMOS chip 18 may include signal filters (e.g., noise reduction), amplifiers, analog to digital convertors, etc. The CMOS chip 18 includes a memory or storage media 104, which may include random access memory (RAM), solid state memory or other memory types.

The memory 104 may store monitored data or act as a buffer for transmission of data by wireless transmission through a transmission port 132 or input/output port 130. Transmission data protocols, handshaking and data transmission are controlled by a data transmission circuit 108. The data transmission circuit 108 transmits data via input/output port 130 or wirelessly through wireless transmission port 132. The wireless transmission port 130 may include an antenna. For low power embodiments, wireless transmission may be performed locally to a nearby recording device or network.

The CMOS chip 18 may include a power management circuit 106. The power management circuit 106 distributes power to the components of the system 10 in accordance with operating priorities. For example, recording heart beats needs for the signals from the MEMS microphone 12 to be recorded. This function may have priority over other system functions. The power management circuit 106 can power down other functions in favor of the monitoring functions. The priorities may be set in advance and may be changed through programming using the input/output port 130. In one embodiment, the power for the system 10 is obtained using an RF source 126 and an electret receiver/antenna 122, which receives the RF energy and converts the energy to a useable current/voltage to power the system 10. The battery-free tag or antenna 122 is employed to harvest energy from RF transmitters 126 to power the system 10. The RF transmitters 126 may include energy from cell phones or dedicated wireless RF transmitters that may be fixed or portable to power the system 10.

The power management circuit 106 can measure the available energy and distribute the energy including storage in a thin battery 120 or other power source to ensure power when an RF source 126 is not available. In other embodiments, power can be stored on the thin battery 120 without the use of other power sources. In other embodiments, other power sources may be employed including photovoltaic cells or other portable sources 124. The power source may include a wearable power source or a remote power source. The power source may be disposable or rechargeable.

The antenna 122, battery 120 and/or photovoltaic cells or other portable sources 124 may be employed together or independently. One or more of these power sources may be present and may be formed of or in the flexible substrate 22.

The CMOS chip 18 may include other circuits and functions. In one example the CMOS chip 18 includes a temperature sensor 110 to monitor a temperature of a chamber or area around the CMOS chip 18. The temperature sensor 110 may include a differential circuit to measure electrical properties between two materials or components to determine expansion/contraction or other temperature dependent properties. The temperature may be stored and/or reported with other data (e.g., heart monitor data).

The MEMS device/microphone 12 may include contacts 26 that touch the skin of the user. The contacts 26 may include a corrosion resistant material or metal. The contacts 26 may also be employed of other purposes, e.g., measuring skin resistance, measuring contact pressure of the system 10, etc. and are electrically connected to the CMOS chip 18 to perform these measurements.

In accordance with the present principles, the system 10 is adhered to a user. Upon activation, the system 10 begins to monitor heartbeat or other bodily sound, e.g., bones cracking, breathing, digestive noise, neck, head, arms, legs or noise from other body parts, etc. The heart sounds, etc. are employed to monitor health, status and/or functionality by analyzing the measured sound wave directly at the user's skin. The MEMS device 12 measures the acoustic waves, which are digitized and recorded or digitized and transmitted by the CMOS chip 18 using one or more ports 130, 132. The wearable system 10 is configured for continuous monitoring of heart or body sounds. The system 10 may be employed for medical monitoring, baseline monitoring, activity monitoring, informational monitoring, etc. A user may have one or more sensors functioning for some period of time to correlate sensor accuracy and precision from one sensor to another or across many sensors at the same time from the same or different locations on the body.

In useful embodiments, one or more systems 10 may be applied to different locations on a user to collect acoustic waves from the user and provide spatial information. In one example, three systems 10 may be placed on a use in different areas. Then, a single sound event may be compared to determine a time of flight to each system 10. Since the time of flight information is known for the three systems 10, a position of a source of the sound can be determined by triangulation methods. Fewer or more systems 10 may be employed to pinpoint a sound source, to collect redundant data sets, etc., as needed. Spatial information may be employed in a plurality of additional ways as well.

Figure 3:
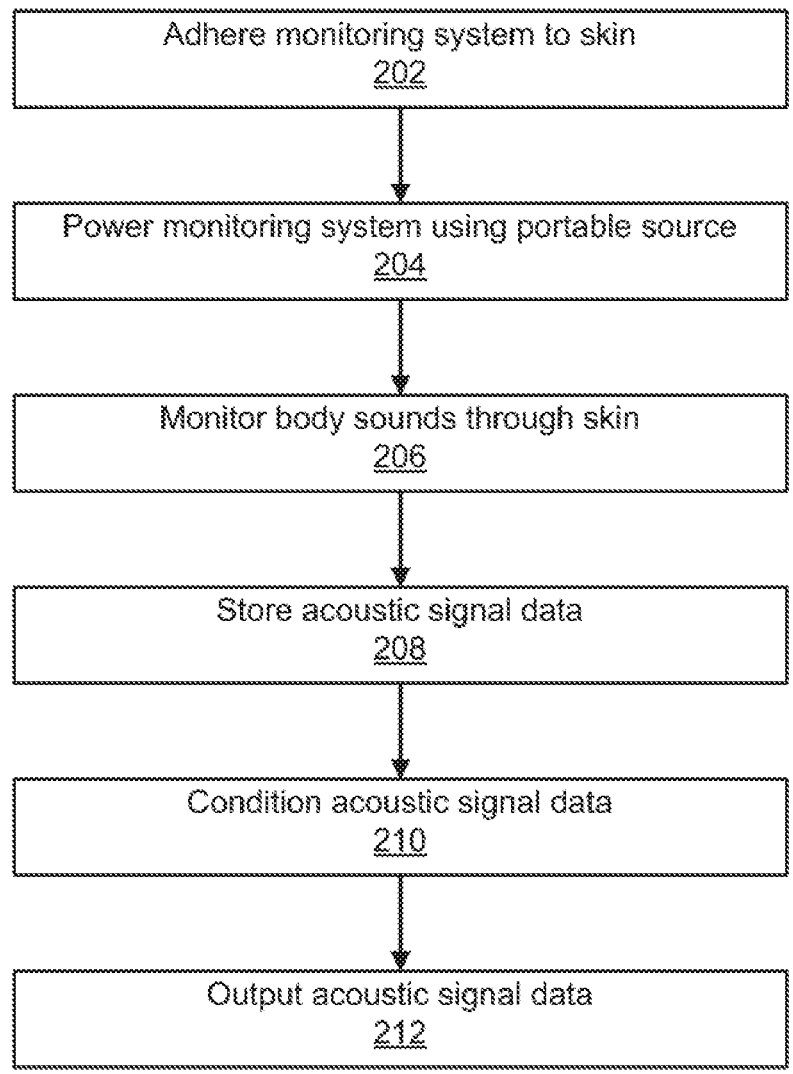
FIG. 3 is a block/flow diagram showing methods for monitoring body sounds in accordance with the present principles.

Referring to FIG. 3, methods for monitoring body sounds are illustratively shown in accordance with the present principles. In block 202, a monitoring system is adhered to skin of a user using a flexible substrate to encapsulate and affix a MEMS microphone to receive acoustic signal data and an integrated circuit chip, which is bonded to and electrically connected to the MEMS microphone.

In block 204, the monitoring system is powered using a portable power source disposed in or on the flexible substrate. The portable power source may include, e.g., a battery-free tag for harvesting energy from radiofrequency signals, a thin battery, a photovoltaic cell, etc.

In block 206, body sounds of the user are monitored through the skin of the user. Other data may also be collected, e.g., temperature, skin resistance, etc. The body sounds may be collected by a plurality of sensor systems for comparison and source location or collection of spatial information. In block 208, the body sounds are stored on the integrated circuit chip. The integrated circuit chip may include memory to store data or to buffer data for wireless or wired transmission.

In block 210, the acoustic signal data or body sounds may be conditioned using a signal processing circuit on the integrated circuit chip. In block 212, data from the monitoring system can be output to a remote device using a wireless transmitter and/or an input/output port. Wireless transmission may occur while the user is wearing the monitoring system in accordance with a wireless protocol (using the data transmission circuit 108). The monitoring system may be plugged into using the input/output port. Data may be read from the monitoring system (while being worn or after being removed) using the input/output port. The data may be transferred to a computer, a network, a cell phone, or any other suitable device. Triangulation methods may be employed to determine where the sounds originated from (e.g., when multiple systems are employed).

Having described preferred embodiments system for continuous, periodic and/or intermittent monitoring of body sounds (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A wearable monitoring system, comprising:
a single microelectromechanical (MEMS) microphone configured to receive acoustic signal data through skin of a user;
an integrated circuit chip bonded to and electrically connected to the MEMS microphone;
a portable power source connected to at least the integrated circuit chip;
a flexible substrate configured to encapsulate and affix the MEMS microphone and the integrated circuit chip to the skin of the user, and forming one or more first sound chambers between the flexible substrate and the skin of the user; and
a second sound chamber forming a gap between a diaphragm and the skin of the user.

2. The system as recited in claim 1, wherein the MEMS microphone includes one of a condenser/electrostatic type device, a piezoelectric type device or piezo-resistive type device.

3. The system as recited in claim 1, wherein the integrated circuit chip is oxide bonded to the MEMS microphone.

4. The system as recited in claim 1, wherein the portable power source includes a battery-free tag formed on or in the flexible substrate for harvesting energy from radiofrequency signals.

5. The system as recited in claim 1, further comprising a transmitter to transmit data from the system to a remote device.

6. The system as recited in claim 1, wherein the integrated circuit chip includes a signal processing circuit configured to condition the acoustic signal data.

7. The system as recited in claim 1, wherein the integrated circuit chip includes memory for storing the acoustic signal data.

8. The system as recited in claim 1, further comprising an input/output port for programming the integrated circuit chip and for outputting data from the integrated circuit chip.

9. The system as recited in claim 1, wherein the system fits within a volume of less than 5 mm by 5 mm by 1.5 mm.

10. The system as recited in claim 1, wherein two or more systems are employed together at different locations on a user to collect acoustic waves and provide spatial information for the acoustic signal data.

11. A wearable monitoring system, comprising:
a single microelectromechanical (MEMS) microphone configured to receive acoustic signal data through skin of a user;
an integrated circuit chip bonded to and electrically connected to the MEMS microphone using flip chip technology;
a flexible substrate configured to encapsulate and affix the MEMS microphone and the integrated circuit chip to the skin of the user using an adhesive, and forming one or more first sound chambers between the flexible substrate and the skin of the user;
a portable power source connected to at least the integrated circuit chip including a battery-free tag formed on or in the flexible substrate for harvesting energy from radiofrequency signals; and
a second sound chamber forming a gap between a diaphragm and the skin of the user.

12. The system as recited in claim 11, wherein the MEMS microphone includes one of a condenser/electrostatic type device, a piezoelectric type device or piezo-resistive type device.

13. The system as recited in claim 11, further comprising a wireless transmitter to transmit data from the system to a remote device.

14. The system as recited in claim 11, wherein the integrated circuit chip includes:
a signal processing circuit configured to condition the acoustic signal data;
memory for storing the acoustic signal data; and
an input/output port for programming the integrated circuit chip and for outputting data from the integrated circuit chip.

15. The system as recited in claim 11, wherein the system fits within a volume of less than 5 mm by 5 mm by 1.5 mm.

16. The system as recited in claim 11, wherein two or more systems are employed together at different locations on a user to collect acoustic waves and provide spatial information for the acoustic signal data.

17. A method for monitoring body sounds, comprising:
adhering a monitoring system to skin of a user using a flexible substrate to encapsulate and affix a single microelectromechanical (MEMS) microphone configured to receive acoustic signal data and an integrated circuit chip, which is bonded to and electrically connected to the MEMS microphone, the flexible substrate forming one or more first sound chambers between the flexible substrate and the skin of the user;
forming a second sound chamber, the second sound chamber being formed by a gap between a diaphragm and the skin of the user;
powering the monitoring system using a portable power source disposed in or on the flexible substrate;
monitoring the acoustic signal data of the user through the skin of the user; and
storing the acoustic signal data on the integrated circuit chip.

18. The method as recited in claim 17, wherein the portable power source includes a battery-free tag for harvesting energy from radio frequency signals.

19. The method as recited in claim 17, further comprising conditioning the acoustic signal data using includes a signal processing circuit on the integrated circuit chip.

20. The method as recited in claim 17, further comprising determining a source of one or more body sounds by employing a plurality of the systems together by affixing each of the systems at different locations on the user, and triangulating a position of the source of the one or more body sounds based on the acoustic signal data from the plurality of systems.

* * * * *